Figure 1:
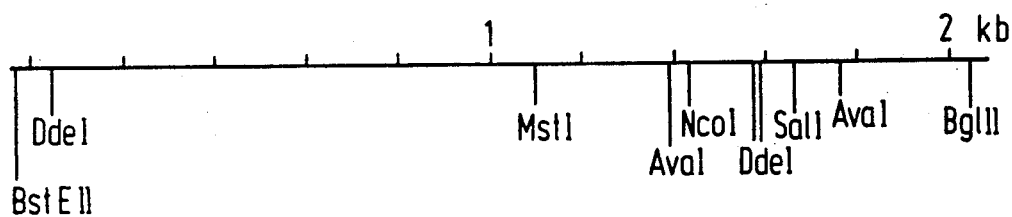

United States Patent [19]

Brauer et al.

[11] Patent Number: 5,077,399
[45] Date of Patent: Dec. 31, 1991

[54] PHOSPHINOTHRICIN-RESISTANCE GENE

[75] Inventors: Dieter Brauer, Flörsheim am Main; Klaus Bartsch, Kelkheim; Günter Donn, Hofheim am Taunus, all of Fed. Rep. of Germany

[73] Assignee: Hoechst Aktiengesellschaft, Frankfurt am Main, Fed. Rep. of Germany

[21] Appl. No.: 515,671

[22] Filed: Apr. 27, 1990

Related U.S. Application Data

[63] Continuation of Ser. No. 193,766, May 13, 1988, abandoned.

[30] Foreign Application Priority Data

May 15, 1987 [DE] Fed. Rep. of Germany ....... 3716309

[51] Int. Cl.$^5$ .................... C12N 15/11; C12N 15/31
[52] U.S. Cl. .................................. 536/27; 435/32.01; 435/252.1; 435/829
[58] Field of Search ................... 435/172.3, 829, 242, 435/317.1, 71.2, 252.1, 253.3, 253.5, 320.1; 935/30, 35, 67; 536/27

[56] References Cited

FOREIGN PATENT DOCUMENTS 0239801 of 0000 European Pat. Off. .
0173327 5/1986 European Pat. Off. .

OTHER PUBLICATIONS

Donn et al., Chemical Abstracts 102(17) 140, Abstract No. 144025, (1985).
Bayer et al., Helvetica Chimica Acta 55(1):224-238, (1972), Abstract.
Bergy's Manual of Systematic Bacteriology, vol. 1, Krieg, ed. Williams and Wilkins, Baltimore, 1984, p. 815.
Murakami et al., (1986), Mol. Gen. Genet. 205:42-50.
Howell et al. (1979), Phytopathology 69:480-482.
Carlson (1973) Science 180:1366-1368.
Leason et al., (1982), Phytochemistry 21:855-857.
Knight et al. (1987), Journal of Bacteriology 169:1954-1959.

*Primary Examiner*—Jacqueline Stone
*Assistant Examiner*—Che S. Chereskin
*Attorney, Agent, or Firm*—Finnegan, Henderson, Farabow, Garrett, and Dunner

[57] ABSTRACT

Phosphinothricin (PTC) selection of bacteria which are not fungus-like yields PTC-resistant selectants. The DNA fragment which carries the resistance gene is obtained from the complete DNA of these selectants by constructing a gene bank and screening for chemical modification of PTC. The resistance gene can be localized to a fragment which is 2 kb in size, and selection for PTC resistance. This gene is suitable for producing PTC-resistant plants and propagation material thereof, and as a resistance marker as well. Microorganisms which contain this PTC-resistance gene can be used in sewage treatment plants.

7 Claims, 1 Drawing Sheet

PHOSPHINOTHRICIN-RESISTANCE GENE

This application is a continuation of application Ser. No. 07/193,766, filed May 13, 1988, now abandoned.

Phosphinothricin (PTC, 2-amino-4-methylphosphinobutyric acid) is an inhibitor of glutamine synthetase. PTC is a "structural unit" of the antiboiotic phosphinothricylalanyl-alanine. This tripeptide (PTT) is active against Gram-positive and Gram-negative bacteria as well as against the fungus Botrytis cinerea (Bayer et al., Helv. chim. Acta 55 (1972) 224). PTT is produced by the strain Streptomyces viridochromogenes Tü 494 (DSM 40736).

The European Patent Application with the publication No. (EP-A) 0,173,327 relates to the biosynthesis of PTT. FIG. 7 makes mention of a resistance gene, which is not characterized in detail, from S. hygroscopicus FERM BP-130 (ATCC 21705).

The Frankfurter Allgemeine Zeitung of Feb. 4, 1987, reports on page 29 (nature and science supplement, top of left-hand column) that it has been possible to isolate from soil bacteria of the genus Streptomyces a gene which is responsible for the breakdown of PTC.

The non-prior-published European Patent Application (EP-A) 0,257,542 proposes a PTC-resistance gene which originates from the abovementioned PTT-producing S. viridochromogenes DSM 40736.

In connection both with the production of PTC and PTT, and with the resistance to these compounds, to date only Streptomycetes have been described or proposed.

Among the bacteria, in many respects the large genus of fungus-like Streptomycetes occupies a special position: Streptomycetes are the most important producers of antibiotics, they form a mycelium which is retained even in the aging colony and often throws out a highly developed aerial mycelium, and in relation to genetic manipulation it is of importance that the ratio of A and T to G and C in their DNA is about 30 to 70.

It has now been found, surprisingly, that other bacteria can also exhibit PTC resistance, especially bacteria which are not fungus-like and are preferably Gram-negative.

German Patent No 2,717,440 discloses that PTC acts as a nonselective or total herbicide. It is distinguished by a short biological half-life in the soil, i.e. in the ground this herbicide is apparently very rapidly modified or broken down by microorganisms, with loss of the herbicidal action. It has been possible to isolate PTC-modifying microorganisms from soil samples which originated from PTC-treated arable land. It has also been possible to select bacteria from sewage sludge for PTC resistance, advantageously after treatment with mutagens.

The invention relates to a phosphinothricin(PTC)-resistance gene obtainable by selection of bacteria, which are not fungus-like, for PTC resistance, extraction of the DNA, construction of a gene bank, isolation of PTC-resistant clones, and isolation of the PTC-resistance gene from these clones.

The invention especially relates to a new PTC-resistance gene which has been obtained from bacteria which are not fungus-like, to cells containing this gene, especially plant cells, and to PTC-resistant plants containing this gene. Another aspect of the invention relates to the use of the gene as a marker in bacterial and plant cells. Further aspects of the invention and preferred embodiments are explained in detail hereinafter.

The gene according to the invention has the restriction map shown in FIG. 1.

Figure 2:
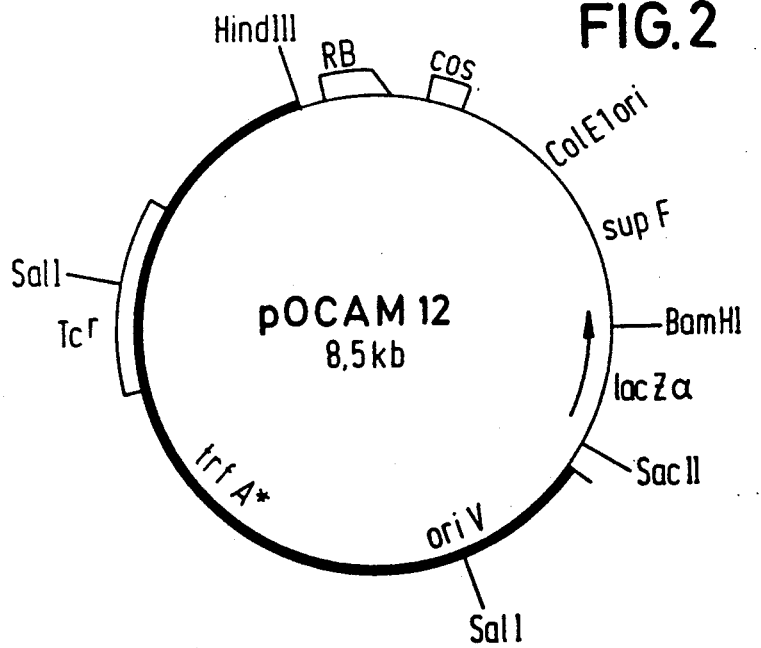

FIG. 2 shows the vector pOCAM 12 which, on construction of a gene bank, can be used for the isolation of the gene shown in FIG. 1.

Selection for PTC-resistant bacteria which are not fungus-like yields, besides uncharacterized microorganisms, essentially asporogenic Gram-negative rods, specifically aerobic organisms of the genus Pseudomonas and pseudo-monad-like bacteria of the genera Alcaligenes and Agrobacterium, as well as the facultative anaerobic enterobacteria of the genera Enterobacter and Serratia, as well as bacteria of the genus Cedecea.

Exact characterization of the PTC-resistant bacterium is unnecessary for the purposes of the invention. It suffices for it to grow adequately in the selection medium which is enriched with PTC.

Once suitable genera and species have been characterized, it is also possible to have recourse to the well-characterized strains of the said species and genera which are available at depositories, and to select from them PTC-resistant strains.

Detailed characterization was carried out on strains of the species Alcaligenes faecalis and eutrophus, Pseudo-monas paucimobilis, Enterobacter agglomerans, Serratia plymuthica, Agrobacterium tumefaciens and Cedecea Gr. V. Based on this knowledge, it is possible, for example, to employ the Alcaligenes strains available from the Deutsche Sammlung von Mikroorganismen (German Microorganism Collection) under the numbers DSM 975 or 30030.

PTC-resistant bacteria of these types, or microorganisms which have been rendered PTC-resistant by introduction of the gene according to the invention, can also be used in sewage treatment plants to break down PTC and its derivatives in manufacturing residues or sewage, or to modify them in such a way that they are broken down by the usual microorganism populations in sewage treatment plants.

In accordance with the proposal in EP-A 0,257,542, the enzyme responsible for the inactivation of PTC has been characterized as glutamic acid N-acetyltransferase. The gene responsible for this activity has been isolated and defined by the restriction map shown in FIG. 1 and the DNA sequence shown in Table 1. This DNA sequence can, of course, also be chemically synthesized by one of the known processes, for example by the phosphite method, it also being possible in a manner known per se to prepare modified genes.

After fusion with suitable host-specific regulator elements, the gene can confer resistance to PTC on other organisms which are inherently PTC-sensitive. This resistance can be used as a selection marker or for obtaining PTC-resistant useful plants.

On treatment of these useful plants with PTC, not only is there the effect that undesired plant growth is inhibited, there is also reduction in undesired microorganisms on the useful plants.

Unless indicated otherwise, percentage data in the examples which follow relate to weight.

EXAMPLE 1

Screening on minimal media and modification assay

The bacteria are extracted from the soil samples using LB medium (10 g of Difco bacto tryptone, 5 g of Difco bacto yeast extract and 10 g of sodium chloride/l), initially cultured overnight, washed with buffer (10 mM Na₂HPO₄/10 mM NaCl), and plated out on selection medium having the following composition:

0.4 g of NaCl, 0.8 g of KH$_2$PO$_4$, 1.6 g of Na$_2$HPO$_4$, 1.6 g of D,L-PTC(NH$_4$), 4 ml of glucose (10%), 0.8 ml of 1 M MgSO$_4$, water to 800 ml;

1.4% agar is added for solid media.

For the modification assay, about 5 ml of bacterial suspension are reduced to a volume of 200 μl and lyzed by addition of 5 μg of lysozyme. After subsequent addition of 1 μCi of 3,4-$^{14}$C-PTC, the mixture is incubated at 28° C. for about 4 h. For the analysis, the mixture is subsequently incubated at 95° C. for 10 min, cooled in ice and centrifuged in a bench centrifuge for 10 min. 10 μl volumes of the clear supernatant are applied to cellulose thin-layer plates (from Merck, Darmstadt, cellulose F, TLC Al foils) which are subjected to ascending chromatography (mobile phase: pyridine, n-butanol, acetic acid and water in the ratio by volume 50 : 75 : 15 : 60), dried and autoradiographed. Under these conditions, the Rf of PTC is about 0.31, and that of N-acetyl-PTC is about 0.33.

For investigation of a cosmid bank, 5 clones are each initially cultured in 5 ml of medium, combined, reduced to a volume of about 300 μl and worked up as described above.

EXAMPLE 2

Preparation of the cosmid vector pOCAM 12

The cosmid vector pOCAM 12 has, because of its ColE1 origin of replication, a high copy number in *E. coli*, and has the wide host range of the naturally occurring plasmid RK2 and a tetracycline-resistance gene. The vector is a derivative of the mobilizable vector pRK404 (G. Ditta et al., Plasmid 13 (1985) 149–153). It can, after uptake of DNA fragments 25 to 40 kb in size, be packaged into λ phages. This vector can be obtained as follows:

The vector pTJS75 (T. S. Schmidhauser and D. R. Helinski, J. Bacteriology 164 (1985) 446–455) is opened with HindIII, and the protruding sequences are made blunt-ended by filling in with DNA polymerase I (Klenow fragment). The vector pSDL 12 (A. Levinson et al., J. Molec. Appl. Genetics 2 (1984) 507–517) is opened with NaeI and SspI, and the large fragment is isolated. The latter and the plasmid pTJS75 which has been linearized and made blunt-ended are now ligated with a blunt-ended BglII segment, which contains the cos region, from pHC79. The right border (RB), which is 23 bp in length, of the Ti plasmid was synthesized and inserted by blunt-ended ligation. The desired plasmid pOCAM 12, which is 8.5 kb in size and is depicted in FIG. 2, is characterized by restriction analysis.

Of course, it is also possible to use for constructing the gene bank another vector, for example one which is commercially available, such as pHC79 (Hohn and Collins, Gene 11 (1980291.).

EXAMPLE 3

Construction of the gene bank

DNA from *Alcaligenes faecalis* is isolated by the method described for eukaryotic DNA (Maniatis et al., Molecular cloning, A Laboratory Manual (1982), pages 280 to 285) and partially cleaved with Sau3AI. The vector pOCAM 12 is digested with BamHI and ligated with DNA fragments about 25–40 kb in size. The ligation and packaging into λ phages are carried out in accordance with the manufacturer's instructions (Amersham: in vitro packaging system for Lambda DNA, Code No. 3342) or as specified by Maniatis et al., pages 296 to 299.

EXAMPLE 4

Infection of the *E. coli* indicator strain DH1, and screening

Bacteria of the strain *E. coli* DH1 are initially cultured in LBMM medium (LB medium plus 2 g of maltose and 2.5 g of magnesium sulfate heptahydrate per liter) to an optical density (OD$_{550}$) of about 1. 200 μl of this suspension are mixed with up to 50 μl of phage suspension, and the mixture is incubated at 37° C. for 30 min. 1 ml of LBMM is added and incubation is continued for 50 min. 100 μl aliquots are streaked onto LB plates supplemented with 10 μg of tetracycline/ml. Single colonies are picked out, initially cultured in 5 ml cultures and examined in groups of 5 as described above. After testing 2,700 cosmid clones, one pool which is examined shows in the autoradiogram the expected signal in the position of N-acetyl-PTC. The clones belonging to this pool are examined singly in the modification assay, and the clone responsible for the modification is identified.

The clone which is found has an insert of about 25,000 to 30,000 bp. It confers resistance to up to about 50 mM PTC on bacteria of the strain *E. coli* DH1 and of the species Agrobacterium tumefaciens and Rhizobium meliloti.

Restriction analysis allows to localize enzymatic activity to an approximately 2 kb BstEII-BglII fragment of the insert. This fragment is characterized by the restriction map (FIG. 1). Further localization and sequencing characterizes the phosphinothricin-resistance gene, whose DNA sequence is depicted in Table 1.

TABLE 1

| 1- Met | Pro | Ser | Ser | Ser | Ser | His | Pro | Ser | Thr | Pro | Asp | Ala | Pro | Gln |
|---|---|---|---|---|---|---|---|---|---|---|---|---|---|---|
| 1- ATG | CCG | TCA | TCT | TCG | TCT | CAC | CCC | TCC | ACT | CCC | GAC | GCG | CCG | CAA |

| 16- Arg | Val | Gly | Val | Glu | Leu | Ala | Arg | Cys | Ala | Cys | Thr | Val | Arg | Val |
|---|---|---|---|---|---|---|---|---|---|---|---|---|---|---|
| 46- CGC | GTC | GGC | GTC | GAA | CTG | GCG | CGT | TGC | GCA | TGC | ACG | GTG | CGC | GTC |

| 31- Val | Arg | Asp | Asp | Asp | Leu | Pro | Ala | Ile | Thr | Ala | Ile | Tyr | Ala | His |
|---|---|---|---|---|---|---|---|---|---|---|---|---|---|---|
| 91- GTG | CGT | GAC | GAC | GAC | CTG | CCC | GCC | ATC | ACG | GCC | ATC | TAC | GCC | CAT |

| 46- His | Val | Arg | Thr | Gly | Thr | Ala | Ser | Phe | Glu | Glu | Val | Pro | Pro | Asp |
|---|---|---|---|---|---|---|---|---|---|---|---|---|---|---|
| 136- CAC | GTG | CGT | ACC | GGC | ACG | GCA | TCG | TTC | GAA | GAG | GTG | CCA | CCC | GAC |

| 61- Asp | Thr | Glu | Met | Arg | Ala | Arg | Cys | Ala | Lys | Val | Leu | Asp | Ala | Gly |
|---|---|---|---|---|---|---|---|---|---|---|---|---|---|---|
| 181- GAC | ACC | GAG | ATG | CGC | GCG | CGT | TGC | GCC | AAG | GTA | CTC | GAC | GCC | GGA |

TABLE 1-continued

```
 76- Leu Pro Tyr Leu Val Ala Glu Arg Asp Gly Lys Leu Leu Gly Tyr
226- CTG CCG TAT CTC GTC GCC GAA CGC GAC GGC AAG CTG CTC GGC TAC

91- Ala Tyr Ala Thr His Tyr Arg Pro Arg Ser Ala Tyr Arg Phe Thr
271- GCA TAC GCC ACG CAT TAC CGG CCG CGC TCC GCC TAC CGT TTC ACG

106- Leu Glu Asp Ser Val Tyr Ile Ala Pro Asp Ala Ile Gly Gln Gly
316- CTG GAA GAC TCG GTG TAT ATC GCC CCC GAT GCG ATC GGG CAG GGC

121- Val Gly Arg Thr Leu Leu Leu Thr Leu Ile Ala Arg Cys Glu Gly
361- GTA GGG CGC ACG CTG TTG CTC ACG CTC ATC GCG CGT TGC GAA GGC

136- Gly Pro Trp Arg Gln Leu Ile Ala Asn Val Gly Asp Ser Gly Asn
406- GGC CCG TGG CGG CAA CTG ATT GCG AAC GTC GGC GAC AGC GGC AAT

151- Thr Ala Ser Leu Gly Leu His Ala Ala Cys Gly Phe Val Gln Ala
451- ACG GCG TCC CTC GGT CTG CAT GCC GCC TGC GGC TTC GTG CAG GCA

166- Gly Val Leu Lys Ser Val Gly Phe Lys Phe Gly Arg Trp Ile Asp
496- GGC GTG CTC AAG TCC GTC GGC TTC AAG TTC GGC CGC TGG ATC GAC

181- Thr Val Leu Met Gln Arg Pro Leu Asn Ala Gly Asp Thr Thr Leu
541- ACG GTG CTC ATG CAA CGG CCG CTC AAC GCG GGC GAC ACA ACG CTG

196- Pro Glu
586- CCG GAG TAA
```

We claim:

1. A phosphinothricin (PTC)-resistance gene obtained by selecting bacteria from the genus Alcaligenes for PTC resistance, extracting the DNA, constructing a gene bank, isolating PTC-resistant clones, and obtaining the PTC-resistance gene from these clones.

2. A gene as claimed in claim 1, wherein bacteria of the species Alcaligenes faecalis or eutropus are selected.

3. A gene as claimed in claim 1, obtained from the complete DNA from bacteria which are of the genus Alcaligenes and have been selected for PTC resistance, bu cutting with BstEII and BglII, cloning of a fragment which is approximately 2 kb in size, and selecting for PTC resistance.

4. A gene as claimed in claim 3, obtained from Alcaligenes faecalis.

5. A gene as claimed in claim 4, which has the restriction map shown in FIG. 1.

6. A substantially pure PTC-resistance gene which has the DNA sequence in Table 1.

7. A gene as claimed in claim 3 wherein bacteria of the species Alcaligenes faecalis or eutrophus are selected.

* * * * *